United States Patent [19]  
Aristoff et al.

[11] Patent Number: 4,533,749  
[45] Date of Patent: Aug. 6, 1985

[54] 9-SUBSTITUTED CARBACYCLIN ANALOGS

[75] Inventors: Paul A. Aristoff, Portage; John C. Sih, Kalamazoo, both of Mich.

[73] Assignee: The Upjohn Company, Kalamazoo, Mich.

[21] Appl. No.: 349,122

[22] Filed: Feb. 16, 1982

[51] Int. Cl.$^3$ ............... C07C 177/00; C07C 57/26
[52] U.S. Cl. .................. 562/501; 564/454; 568/633; 260/404; 568/734; 568/819; 260/404.5; 260/408; 260/410; 260/410.9 R; 260/413; 260/464; 260/465 R; 549/79; 549/501; 560/12; 560/39; 560/45; 560/56; 560/119; 562/427; 562/444; 562/455; 562/466; 564/88; 564/89; 564/91; 564/96; 564/97; 564/98; 564/99; 564/152; 564/158; 564/159; 564/172; 564/188; 564/428
[58] Field of Search ............... 560/119, 12, 39, 45, 560/56; 562/501, 427, 444, 455, 406; 564/88, 89, 91, 96, 97, 98, 99, 152, 158, 159, 172, 188, 428, 454; 568/633, 734, 819; 260/404, 404.5, 408, 410, 410.9 R, 413, 464, 465

[56] References Cited

U.S. PATENT DOCUMENTS

| 4,057,571 | 11/1977 | Grudzinskas | 560/121 |
| 4,180,657 | 12/1979 | Sih | 542/426 |
| 4,192,891 | 3/1980 | Haslanger | 424/305 |
| 4,225,508 | 9/1980 | Sih | 260/346.22 |
| 4,238,414 | 12/1980 | Morton, Jr. | 564/453 |
| 4,306,075 | 12/1981 | Aristoff | 560/56 |
| 4,306,076 | 12/1981 | Nelson | 560/56 |
| 4,420,632 | 12/1983 | Aristoff | 560/119 |

FOREIGN PATENT DOCUMENTS

| 2900352 | 7/1979 | Fed. Rep. of Germany . | |
| 2845770 | 4/1980 | Fed. Rep. of Germany | 560/119 |
| 4024865 | 2/1979 | Japan . | |
| 4063059 | 5/1979 | Japan . | |
| 4063060 | 5/1979 | Japan . | |
| 2012265 | 7/1979 | United Kingdom . | |
| 2013661 | 8/1979 | United Kingdom . | |
| 2017699 | 10/1979 | United Kingdom . | |

OTHER PUBLICATIONS

Story, J. Am. Chem. Soc., 98, 1583 (1976).
Aristoff, P. A., J. Org. Chem., 46 (No. 9), 1981, pp. 1954–1957, "Practical Synthesis of 6a-Carbaprostaglandin I$_2$".
Barco, A., et al., J. Org. Chem., 45 (No. 23), 1980, pp. 4776–4778, "A New, Elegant Route to a Key Intermediate for the Synthesis of 9(O)-Methanoprostacyclin".
Hayashi, M., et al., Chem. Lett., 1979, pp. 1437–1440, "A Synthesis of 9(O)-Methanoprostacyclin".
Kojima, K., et al., Tetrahedron Lett., 39, 1978, pp. 3743–3746, "Total Synthesis of 9(O)-Methanoprostacyclin and its Isomers".
Morton, D. R., Jr., et al., J. Org. Chem., 44 (No. 16), 1979, pp. 2880–2887, "Total Synthesis of 6a-Carbaprostaglandin I$_2$ and Related Isomers".
Nicolaou, K. C., et al., J.C.S. Chem. Comm., 1978, pp. 1067–1068, "Total Synthesis of Carboprostacyclin, a Stable and Biologically Active Analogue of Prostacyclin(PGI$_2$)".
Shibasaki, M., et al., Chem. Lett., 1979, pp. 1299–1300, "A Stereo and Regiospecific Route to the Synthetic Intermediate for the Synthesis of 9(O)-Methanoprostacyclin".
Shibasaki, M., et al., Tetrahedron Lett., 5, 1979, pp. 433–436, "New Synthetic Routes to 9(O)-Methanoprostacyclin. A Highly Stable and Biologically Potent Analog of Prostacyclin".
Skuballa, W., et al., Angew. Chem., 93 (No. 12), 1981, pp. 1080–1081, "Ein neuer Weg zu 6a-Carbacyclinen-Synthese eines stabilen, biologisch potenten Prostacyclin-Analogons".
Sugie, A., et al., Tetrahedron Lett., 28, 1979, pp. 2607–2610, "Stereocontrolled Approaches to 9(O)-Methanoprostacyclin".
Yamazaki, M., et al., Chem. Lett., 1981, pp. 1245–1248, "1,2-Carbonyl Transposition of cis-Bicyclo[3.3.0]octan-2-one to its 3-one Skeleton: Application to Syntheses of d1-Hirsutic Acid and d1-9(O)-Methanoprostacyclin".

Primary Examiner—Robert Gerstl
Attorney, Agent, or Firm—L. Ruth Hattan

[57] ABSTRACT

Novel compounds of the following general formula:

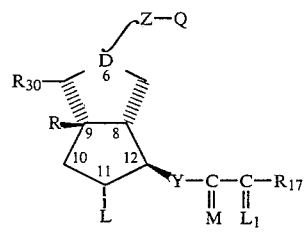

9 Claims, No Drawings

9-SUBSTITUTED CARBACYCLIN ANALOGS

BACKGROUND OF THE INVENTION

The present invention relates to novel compounds which are 9-substituted carbacyclin analogs, to processes for the preparation of said carbacyclin analogs and the use of said analogs as pharmacological agents or as intermediates for the preparation of compounds useful as pharmacological agents. This invention also relates to chemical intermediates for preparing the novel 9-substituted carbacycl in compounds described and claimed herein.

Prostacyclin is an endogenously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "$PGI_2$". Carbacyclin, 6a-carba-$PGI_2$, exhibits the structure and carbon atom numbering indicated in formula II when the C-5,6 positions are unsaturated. Likewise, for convenience, carbacyclin is referred to simply as "$CBA_2$".

A stable partially saturated derivative of $PGI_2$ is $PGI_1$ or 5,6-dihydro-$PGI_2$ when the C-5,6 positions are saturated, depicted with carbon atom numbering in formula I when the C-5,6 positions are saturated. The corresponding 5,6-dihydro-$CBA_2$ is $CBA_1$, depicted in formula II when the C-5,6 positions are saturated.

As is apparent from inspection of formulas I and II, prostacyclin and carbacyclin may be trivially named as derivatives of PGF-type compounds, e.g., $PGF_{2\alpha}$ of formula III. Accordingly, prostacyclin is trivially named 9-deoxy-6,9α-epoxy-(5Z)-5,6-didehydro-$PGF_1$ and carbacyclin is named 9-deoxy-6,9α-methano-(5Z)-5,6-didehydro-$PGF_1$. For description of prostacyclin and its structural identification, see Johnson, et al, Prostaglandins 12:915 (1976).

In naming the novel compounds of the present invention in general the art-recognized system of nomenclature described by N. A. Nelson, J. Med. Chem. 17:911 (1974) for prostaglandins is followed. As a matter of convenience, however, the novel carbacyclin derivatives herein are named as 6a-carba-prostaglandin $I_2$ compounds, or as $CBA_1$ or $CBA_2$ derivatives.

In the formulas herein, broken line attachments to a ring indicate substituents in the "alpha" ($\alpha$) configuration, i.e., below the plane of said ring. Heavy solid line attachments to a ring indicate substituents in the "beta" ($\beta$) configuration, i.e., above the plane of said ring. The use of wavy lines ($\sim$) herein will represent attachment of substituents in the alpha or beta configuration or attached in a mixture of alpha and beta configurations. Alternatively wavy lines will represent either an E or Z geometric isomeric configuration or the mixture thereof. Also, solid and dotted lines used together, as for example, in formulas I and II at C-5,6 positions indicates the presence of either a double bond or alternatively a single bond.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel carbacyclin analogs herein. Molecules of carbacyclin have several centers of asymmetry and therefore can exist in optically inactive form or in either of two enantiomeric (optically active) forms, i.e., the dextrorotatory and laveorotatory forms. The racemic form of carbacyclin contains equal numbers of both enantiomeric molecules. For convenience, reference to carbacyclin or $CBA_2$ or $CBA_1$ will refer to the optically active form thereof.

A formula as drawn herein which depicts a prostacyclin-type product or an intermediate useful in the preparation thereof, represents that particular stereoisomer of the prostacyclin-type product which is of the same relative stereochemical configuration as prostacyclin obtained from mammalian tissues or the particular stereoisomer of the intermediate which is useful in preparing the above stereoisomer of the prostacyclin type product. As drawn, formula I corresponds to that of $PGI_2$ endogenously produced in the mammalian species. In particular, refer to the stereochemical configuration at C-8 ($\alpha$), C-9 ($\alpha$), C-11 ($\alpha$) and C-12 ($\beta$) of endogenously produced prostacyclin. The mirror image of the above formula for prostacyclin represents the other enantiomer.

The term "prostacyclin analog" or "carbacyclin analog" represents that stereoisomer of a prostacyclin-type product which is of the same relative stereochemical configuration as prostacyclin obtained from mammalian tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia 63,059 and 63,060, also abstracted respectively as Derwent Farmdoc CPI Numbers 48154B/26 and 48155B/26. See also British published specifications 2,012,265 and German Offenlungsschrift 2,900,352, abstracted as Derwent Farmdoc CPI Number 54825B/30. See also British published applications 2,017,699 and 2,013,661 and U.S. Pat. No. 4,238,414. The synthesis of carbacyclin and related compounds is also reported in the chemical literature, as follows: Morton, D.R., et al, J. Org. Chem. 44:2880–2887 (1979); Shibasaki, M., et al, Tetrahedron Lett., 433–436 (1979); Kojima, K., et al, Tetrahedron Lett., 3743–3746 (1978); Nicolaou, K.C., et al, J. Chem. Soc. Chemical Communications, 1067–1068 (1978); Sugie, A., et. al., Tetrahedron Lett., 2607–2610 (1979); Shibasaki, M., Chem. Lett., 1299–1300 (1979), and Hayashi, M., Chem. Lett., 1437–40 (1979); Aristoff, P.A., J. Org. Chem. 46, 1954–1957 (1981); Yamazaki, M., et al, Chem. Lett., 1245–1248 (1981); and Barco, A., et al, J. Org. Chem. 45, 4776–4778 (1980); and Skuballa, W., et al, Angew. Chem. 93, 1080–1081 (1981). 7-Oxo and 7-hydroxy-$CBA_2$ compounds are apparently disclosed in U.S. Pat. No. 4,192,891. 19-Hydroxy-$CBA_2$ compounds are disclosed in United States Serial No. 054,811, filed 5 July 1979. $CBA_2$ aromatic esters are disclosed in U.S. Pat. No. 4,180,657. 11-Deoxy-$\Delta^{10}$-or $\Delta^{11}$-$CBA_2$ compounds are described in Japanese Kokai 77/24,865, published 24 Feb. 1979. Related 9β-substituted compounds are disclosed in U.S. Pat. Nos. 4,306,075 and 4,306,076.

SUMMARY OF THE INVENTION

The present invention consists of compounds of formula IV wherein R is $C_1$-$C_4$alkyl; $R_{30}$ is hydrogen or $R_{30}$ and R taken together form a methylene moiety, i.e., —$CH_2$—;

wherein D is cis-C=C($R_3$)—, trans—C=C($R_3$)— or >CHCH$_2$, wherein $R_3$ is hydrogen or fluoro;

wherein Z is:
(1) —$CH_2$—($CH_2$)$_f$—C($R_4$)$_2$—wherein each $R_4$ is the same and is hydrogen or fluoro, and f is zero, one, 2 or 3;
(2) trans—$CH_2CH=CH$—; or
(3) —(Ph)—($CH_2$)$_g$—wherein Ph is 1,2—, 1,3—, or 1,4-phenylene and g is zero, one, 2 or 3; with the proviso that when Z is —(Ph)—($CH_2$)$_g$—, $R_3$ is hydrogen;

wherein Q is
(1) —COO$R_5$, wherein $R_5$ is
   (a) hydrogen,
   (b) ($C_1$-$C_{12}$)alkyl,
   (c) ($C_3$-$C_{10}$)cycloalkyl,
   (d) ($C_7$-$C_{12}$)aralkyl,
   (e) phenyl optionally substituted with one, 2 or 3 chloro or ($C_1$-$C_4$)alkyl,
   (f) phenyl substituted in the para-position with —NHCO$R_6$, —CO$R_7$, —OC(O)$R_8$ or —CH=N—NHCONH$_2$, wherein $R_6$ is methyl, phenyl, acetamidophenyl, benzamidophenyl or —NH$_2$; $R_7$ is methyl, phenyl, —NH$_2$, or methoxy; and $R_8$ is phenyl or acetamidophenyl;
   (g) phthalidyl,
   (h) 3-(5,5-dimethyl-1,3,2-dioxaphosphorinan-2-yl)-2-oxopropan-1-yl P-oxide,
   (i) 3-(5,5-di(hydroxymethyl)-1,3,2-dioxaphosphorinan-2-yl)-2-oxopropan-1-yl P-oxide, or
   (j) a pharmacologically acceptable cation;
(2) —$CH_2OH$;
(3) —$COL_2$, wherein $L_2$ is
   (a) an amino group of the formula —$NR_9R_{10}$ wherein $R_9$ is hydrogen or ($C_1$-$C_{12}$)alkyl and $R_{10}$ is
      (i) hydrogen
      (ii) ($C_1$-$C_{12}$)alkyl
      (iii) ($C_3$-$C_{10}$)cycloalkyl,
      (iv) ($C_7$-$C_{12}$)aralkyl
      (v) phenyl optionally substituted with one, 2 or 3 chloro, ($C_1$-$C_3$)alkyl, hydroxy, carboxy, ($C_2$-$C_5$)alkoxycarbonyl, or nitro,
      (vi) ($C_2$-$C_5$)carboxyalkyl,
      (vii) ($C_2$-$C_5$)carbamoylalkyl,
      (viii) ($C_2$-$C_5$)cyanoalkyl,
      (ix) ($C_3$-$C_6$)acetylalkyl,
      (x) ($C_7$-$C_{12}$)benzoalkyl, optionally substituted by one, 2, or 3 chloro, ($C_1$-$C_3$)alkyl, hydroxy, ($C_1$-$C_3$)alkoxy, carboxy, ($C_2$-$C_5$)alkoxycarbonyl, or nitro,
      (ix) pyridyl, optionally substituted by one, 2, or 3 chloro, ($C_1$-$C_3$)alkyl, or ($C_1$-$C_3$)alkoxy,
      (xii) ($C_6$-$C_9$)pyridylalkyl optionally substituted by one, 2, or 3 chloro, ($C_1$-$C_3$)alkyl, hydroxy, or ($C_1$-$C_3$)alkyl,
      (xiii) ($C_1$-$C_4$)hydroxyalkyl,
      (xiv) ($C_1$-$C_4$)dihydroxyalkyl,
      (xv) ($C_1$-$C_4$)trihydroxyalkyl;
   (b) cycloamine selected from the group consisting of pyrolidino, piperidino, morpholino, piperazino, hexamethyleneimino, pyrroline, or 3,4-didehydropiperidinyl optionally substituted by one or 2 ($C_1$-$C_{12}$)alkyl;
   (c) carbonylamino of the formula —$NR_{11}COR_{10}$, wherein $R_{11}$ is hydrogen or ($C_1$-$C_4$)alkyl and $R_{10}$ is other than hydrogen, but otherwise defined as above;
   (d) sulfonylamino of the formula —$NR_{11}SO_2R_{10}$, wherein $R_{11}$ and $R_{10}$ are defined in (c);
(4) —$CH_2NL_3L_4$, wherein $L_3$ and $L_4$ are hydrogen or ($C_1$-$C_4$)alkyl, being the same or different, or the pharmacologically acceptable acid addition salts thereof when Q is —$CH_2NL_3L_4$; or
(5) —CN;

wherein L is H,H; $\alpha$—$OR_{12}$,$\beta$—H,$\beta$—$OR_{12}$; $\alpha$—$CH_2OR_{12}$, $\beta$—H; $\alpha$—H,$\beta$—$CH_2OR_{12}$ wherein $R_{12}$ is hydrogen or a hydroxyl protecting group;

wherein Y is trans —CH=CH—, cis—CH=CH—, —$CH_2CH_2$—, or —C≡C—;

wherein M is $\alpha$—$OR_{12}$, $\beta$—$R_{14}$ or $\alpha$-$R_{14}$, $\beta$—$OR_{12}$; wherein $R_{12}$ is as defined above, and $R_{14}$ is hydrogen or methyl;

wherein $L_1$ is $\alpha$—$R_{15}$,$\beta$—$R_{16}$; $\alpha$—$R_{16}$, $\beta$—$R_{15}$; or a mixture thereof wherein $R_{15}$ and $R_{16}$ are hydrogen, methyl, or fluoro being the same or different with the proviso that one of $R_{15}$ and $R_{16}$ is fluoro only when the other of $R_{15}$ and $R_{16}$ is hydrogen or fluoro;

wherein $R_{17}$ is

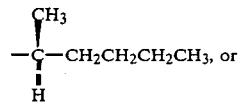

wherein taken together is

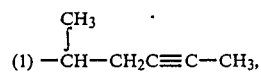

(2) —C≡C—$C_qH_{2q}CH_3$ wherein q is an integer of from 2 to 6, or
(3) —$C_pH_{2p}CH=CH_2$ wherein p is an integer of from 3 to 7;

and individual optical isomers thereof.

The compounds of Formula V, which are useful as intermediates in the preparation of the compounds of Formula IV, are also a part of the present invention. In Formula V the substituent groups L, Y, M, $L_1$, $R_{17}$, s, $R_{30}$ and R have the same meanings as defined in Formula IV.

In the compounds of the present invention, and as used herein, (---) denotes the $\alpha$-configuration, (◄) denotes the $\beta$-configuration, ($\sim$) denotes $\alpha$- and/or $\beta$-configuration or the E and/or Z isomer.

With regard to the divalent groups described above, i.e., M, L and $L_1$ said divalent groups are defined in terms of an $\alpha$-substituent and a $\beta$-substituent which means that the $\alpha$-substituent of the divalent group is in the alpha configuration with respect to the plane of the C-8 to C-12 cyclopentane ring and the $\beta$-substituent is in the beta configuration with respect to said cyclopentane ring.

The carbon atoms content of various hydrocarbon containing groups is indicated by a prefix designating the minimum and maximum number of carbon atoms in the moiety. For example, in defining the moiety $L_2$ in the $-COL_2$ substituent group the definition $(C_1-C_{12})$alkyl means that $L_2$ can be an alkyl group having from one to 12 carbon atoms. Additionally, any moiety so defined includes straight chain or branched chain groups. Thus $(C_1-C_{12})$alkyl as set forth above includes straight or branched chain alkyl groups having from 1 to 12 carbon atoms and as additional illustration, when $L_2$ represnts, for example, $(C_2-C_5)$carboxyalkyl, the alkyl moiety thereof contains from 1 to 4 carbon atoms and is a straight chain or a branched chain alkyl group.

The compounds of the present invention exhibiting the olefinic double bond at C-5,6 positions are $CBA_2$ compounds, while compounds which are saturated at the C-5,6 positions are $CBA_1$ compounds.

Novel compounds wherein Z is $-(Ph)-(CH_2)_g-$ are designated inter-o-, inter-m-, or inter-p-phenylene depending on whether the attachment between C-5 and the $-(CH_2)_g-$ moiety is ortho, meta, or para, respectively. For those compounds wherein g is zero, one or 2, the carbacyclin analogs so described are further characterized as 2,3,4-trinor, 3,4-dinor-, or 4-nor, since in this event the Q-terminated side chain contains (not including the phenylene) 2, 3, or 4 carbon atoms, respectively, in place of the five carbon atoms contained in $PGI_2$. The missing carbon atom or atoms are considered to be at the C-4 to C-2 positions such that the phenylene is connected to the C-5 and C-1 to C-3 positions. Accordingly these compounds are named as 1,5-, 2,5-, and 3,5-inter-phenylene-CBA compounds when g is zero, one, or 2, respectively and when g is 3 the compounds are named as 4,5-inter-phenylene-CBA compounds.

Those CBA analogs wherein Z is $-CH_2-(CH_2-)_f-C(R_4)_2-$ wherein $R_4$ is fluoro are characterized as "2,2-difluoro-" compounds. For those compounds wherein f is zero, 2, or 3, the carbacyclin analogs so described are further characterized as 2-nor, 2a-homo, or 2a,2b-di-homo, since in this event the Q-terminated side chain contains 4, 6, or 7 carbon atoms, respectively, in place of the five carbon atoms contained in $PGI_2$. The missing carbon atom is condsidered to be at the C-2 position such that the C-1 carbon atom is connected to the C-3 position. The additional carbon atom or atoms are considered as though they were inserted between the C-2 and C-3 positions. Accordingly these additional carbon atoms are referred to as C-2a and C-2b, counting from the C-2 to the C-3 position.

Those CBA analogs wherein Z is trans-$CH_2-CH=CH-$ are described as "trans-2,3-didehydro-CBA" compounds.

Those novel compounds where s is 2 are further characterized as 7a-homo-CBA compounds by virtue of the cyclohexyl ring replacing the heterocyclic ring of prostacyclin.

Further, all of the novel compounds of the present invention contain a substituent at the 9β-position and are named as 9β-substituted or 6aβ,9β-methano substituted compounds.

When $R_3$ is fluoro, 5-fluoro-" compounds are described.

When $R_{14}$ is methyl, the carbacyclin analogs are all named as "15-methyl-" compounds. Further, except for compounds wherein Y is cis$-CH=CH-$, compounds wherein the M moiety contains an hydroxyl in the beta configuration are additionally named as "15-epi-" compounds.

For the compounds wherein Y is cis$-CH=CH-$, then compounds wherein the M moiety contains an hydroxyl in the alpha configuration are named as "--epi-CBA" compounds. For a description of this convention of nomenclature for identifying C-15 epimers, see U.S. Pat. No. 4,016,184, issued 5 April 1977, particularly columns 24-27 thereof.

The novel carbacyclin analogs herein which contain $-(CH_2)_2-$, cis$-CH=CH-$, or $-C\equiv C-$ as the Y moiety, are accordingly referred to as "13,14-dihydro", "cis-13", or "13,14-didehydro" compounds, respectively.

When $R_{17}$ is

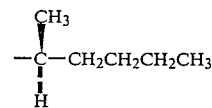

the compounds so described are named as 17(S),20-dimethyl compounds.

When $-C(L_1)-R_{17}$ is

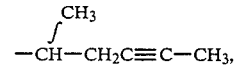

the compounds are named as "16-(R,S)methyl-18,19-tetradehydro" compounds.

When $-C(L_1)R_{17}$ is $-C\equiv C-C_qH_{2q}CH_3$ wherein q is an integer of from 2 to 6 compounds so described are named as "16,17-tetradehydro", "16,17-tetradehydro-20-methyl", "16,17-tetradehydro-20-ethyl", "16,17-tetrahydro-20-n-propyl" and "16,17-tetrahydro-20-n-butyl" compounds as the integer as represented by q varies from 2 to 6 respectively.

When $-C(L_1)R_{17}$ is $-C_pH_{2p}CH=CH_2$ wherein p is an integer of from 3 to 7 the compounds so described are named as "19,20-didehydro", "19,20-didehydro-18a, 18b-dihomo", "19,20-didehydro-18a, 18b, 18c-trihomo", "19,20-didehydro-18a, 18b, 18c, 18d-tetrahomo" compounds as the integer represented by p varies from 3 to 7 respectively.

When at least one of $R_{15}$ and $R_{16}$ is not hydrogen then there are described the "16-methyl" (one and only one of $R_{15}$ and $R_{16}$ is methyl), "16,16-dimethyl" ($R_{15}$ and $R_{16}$ are both methyl), "16-fluoro" (one and only one of $R_{15}$ and $R_{16}$ is fluoro), "16,16-difluoro" ($R_{15}$ and $R_{16}$ are both fluoro) compounds. For those compounds wherein $R_{15}$ and $R_{16}$ are different, the carbacyclin analogs so represented contain an asymmetric carbon atom at C-16. Accordingly, two epimeric configurations are possible: "(16S)" and "(16R)". Further, there is described by this invention the C-16 epimeric mixture: "(16RS)".

When Q is $-CH_2OH$, the compounds so described are named as "2-decarboxy-2-hydroxymethyl" compounds.

When Q is $-CH_2NL_3L_4$, the compounds so described are named as "2-decarboxy-2-aminomethyl" or "2-(substituted amino)methyl" compounds.

When Q is $-COL_2$, the novel compounds herein are named as amides. Further, when Q is $-COOR_5$ and $R_5$ is other than hydrogen the novel compounds herein are named as esters and salts.

When Q is CN the novel compounds herein are named as 2-decarboxy-2-cyano compounds.

Examples of phenyl esters substituted in the para position (i.e., Q is —COOR$_5$, R$_5$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is —COL$_2$) include the following:

(1) Amides within the scope of alkylamino groups of the formula-NR$_9$R$_{10}$ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further isopropylamide, di-n-butylamide, methylethylamide, di-tert-butylamide, methylpropylamide, methylbutylamide, ethylpropylamide ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tertbutylcyclopentylamide, cyclohexylamide, 4-tertbutylcyclohexylamide, 3-isopropylcyclohexlamide, 2,2-dimethylcyclohexlamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N benzyl-amide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethyoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)-propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ- dihydroxybutyl-amide, γ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula —$NR_{11}COR_{10}$ are methylcarbonylamide, ethylcarbonylamide, phenylcarbonylamide, and benzylcarbonylamide.

(4) Amides within the scope of sulfonylamino of the formula —$NR_{11}COR_{10}$ are methysulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tert-butyl, isopentyl, neopentyl, butyl, pentyl, hexyl, heptyl, octyl, nonyl, decyl, undecyl, dodecyl, isomeric forms thereof.

Examples of ($C_3$–$C_{10}$)cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tertbutylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of ($C_7$–$C_{12}$)aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl), 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

The terms phthalidyl; 3-(5,5-dimethyl-1,3,2-dioxaphosphorinan-2-yl)-2-oxopropan-1-yl P-oxide; and 3-(5,5-di(hydroxymethyl)- 1,3,2-dioxaphosphorinan-2-yl)-2-oxopropan-1-yl P-oxide; which $R_5$ may represent in the —$COOR_5$ group mean the following respective moieties (a), (b) and (c):

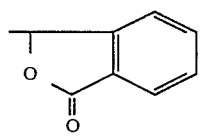

(a)

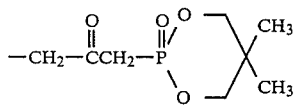

(b)

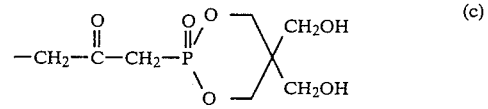

(c)

As indicated hereinabove $R_{12}$ is hydrogen or a protecting group. Those protective groups within the scope of $R_{12}$ are any group which replaces a hydroxy hydrogen and is neither attacked by nor is reactive to the reagents used in the transformations used herein as a hydroxy is and which is subsequently replaceable by hydrolysis with hydrogen in the preparation of the carbacyclin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pp. 51–79 (1969). Those blocking groups which have been found useful include:

(a) tetrahydropyranyl;
(b) tetrahydrofuranyl;
(c) a group of the formula —$C(OR_{24})(R_{18})$—$CH(R_{19})(R_{20})$, wherein $R_{24}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{18}$ and $R_{19}$ are alkyl of one to 4 carbon atoms, inclusive, phenyl, phenyl substituted with one, 2 or 3 alkyl of one to 4 carbon atoms, inclusive, or when $R_{18}$ and $R_{19}$ are taken together —$(CH_2)_a$— or when $R_{18}$ and $R_{19}$ are taken together to form —$(CH_2)_b$—O—$(CH_2)_c$, wherein a is 3, 4, or 5 and b is one, 2, or 3, and c is one, 2, or 3, with the proviso that b plus c is 2, 3, or 4, with the further proviso that $R_{18}$ and $R_{19}$ may be the same or different, and wherein $R_{20}$ is hydrogen or phenyl; and
(d) silyl groups according to $R_{21}$, as qualified hereinafter.

When the protective group $R_{12}$ is tetrahydropyranyl, the tetrahydropyranyl ether derivative of any hydroxy moieties of the CBA-type intermediates herein is obtained by reaction of the hydroxy-containing compound with 2,3-hydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the $R_{12}$ protective group is tetrahydrofuranyl, 2,3-dihydrofuran is used, as described in the preceding paragraph, in place of the 2,3-dihydropyran.

When the $R_{12}$ protective group is of the formula —$C(OR_{24})(R_{18})$—$CH(R_{19})(R_{20})$, wherein $R_{24}$, $R_{18}$, $R_{19}$, and $R_{20}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

$R_{21}$ is a silyl protective group of the formula —$Si(G_1)_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of $-Si(G_1)_3$ include trimethylsilyl, dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to $R_{12}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The protective groups as defined by $R_{12}$ are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

$R_{13}$ is a hydroxyl protective group, as indicated above. As such, $R_{13}$ may be an acyl protective group according to $R_{22}$ as defined below, an acid hydrolyzable protective group according to $R_{12}$ as defined above, a silyl protective group according to $R_{21}$ as defined above, or an arylmethyl protecting group as defined below as substituent $R_1$.

Acyl protecting groups according to $R_{22}$ include:
(a) benzoyl;
(b) benzoyl substituted with one to 5 alkyl of one to 4 carbon atoms, inclusive, or phenylalkyl of 7 to 12 carbon atoms, inclusive, or nitro, with the proviso that not more than two substituents are other than alkyl, and that the total number of carbon atoms in the substituents does not exceed 10 carbon atoms, with the further proviso that the substituents are the same or different;
(c) benzoyl subsituted with alkoxycarbonyl of 2 to 5 carbon atoms, inclusive;
(d) naphthoyl;
(e) naphthoyl substituted with one to 9, inclusive, alkyl of one to 4 carbon atoms, inclusive, phenylalkyl of 7 to 10 carbon atoms, inclusive, or nitro, with the proviso that not more than two substituents on either of the fused aromatic rings are other than alkyl and that the total number of carbon atoms in the substituents on either of the fused aromatic rings does not exceed 10 carbon atoms, with the futher proviso that the various substituents are the same or different; or
(f) alkanoyl of 2 to 12 carbon atoms, inclusive.

In preparing these acyl derivatives of a hydroxy-containing compound herein, methods generally known in the art are employed. Thus, for example, an aromatic acid of the formula $R_{22}OH$, wherein $R_{22}$ is as defined above (e.g., $R_{22}OH$ is benzoic acid), is reacted with the hydroxy-containing compound in the presence of a dehydrating agent, e.g. p-toluensulfonyl chloride or dicyclohexylcarbodiimide; or alternatively an anhydride of the aromatic acid of the formula $(R_{22})OH$, e.g., benzoic anhydride, is used.

Preferably, however, the process described in the above paragraph proceeds by use of the appropriate acyl halide, e.g., $R_{22}Hal$, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_{22}$, the following compounds are available as acids $(R_{22}OH)$, $(R_{22})_2O$, or acyl chlorides $(R_{22}Cl)$: benzoyl; substituted benzoyl, e.g., (2-, 3-, or 4-)methylbenzoyl, (2-, 3-, or 4-)ethylbenzoyl, (2-, 3-, or 4-)isopropylbenzoyl, (2-, 3-, or 4-)tertbutylbenzoyl, 2,4-dimethylbenzoyl, 3,5-dimethylbenzoyl, 2-isopropyltoluyl, 2,4,6-trimethylbenzoyl, pentamethylbenzoyl, phenyl(2-, 3-, or 4-)toluyl, (2-, 3-, or 4-)phenethylbenzoyl, (2'-, 3-, or 4-)nitrobenzoyl, (2,4, 2,5-, or 2,3-)dinitrobenzoyl, 2,3-dimethyl-2-nitrobenzoyl, 4,5-dimethyl-2-nitrobenzoyl, 2-nitro-6-phenylethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; subsituted naphthoyl, e.g., (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)-methyl-1-naphthoyl, 4-ethyl-2-naphthoyl, and (5- or 8-)nitro-2-naphthoyl and acetyl.

There may be employed, therefore, benzoyl chloride, 4-nitrobenzoyl chloride, 3,5-dinitrobenzoyl chloride, or the like, i.e. $R_{22}Cl$ compounds corresponding to the above $R_{22}$ groups. If the acyl chloride is not available, it is prepared from the corresponding acid and phosphorus pentachloride as is known in the art. It is preferred that the $R_{22}OH$, $(R_{22})_2O$, or $R_{22}Cl$ reactant does not have bulky hindering substitutents, e.g. tert-butyl on both of the ring carbon atoms adjacent to the carbonyl attaching site.

The acyl protective groups, according to $R_{22}$, are removed by deacylation. Alkali metal carbonate or hydroxide are employed effectively at ambient temperature for this purpose. For example, potassium carbonate or hydroxide in aqueous methanol at about 25° C. is advantageously employed.

$R_1$ is any arylmethyl group which replaces the hydroxy hydrogen of the intermediates in the preparation of the various CBA analogs herein which is subsequently replaceable by hydrogen in the processes herein for preparation of these respective carbacyclin analogs, being stable with respect to the various reactions to which $R_{13}$-containing compounds are subjected and being introduced and subsequently removed by hydrogenolysis or by treatment with liquid ammonia in an ether solvent such as diethyl ether in the presence of a strong base such as an alkyl lithium.

Examples of arylmethyl protecting groups are
(a) benzyl;
(b) benzyl substituted by one to 5 alkyl of one to 4 carbon atoms inclusive, chloro, bromo, iodo, fluoro, nitro, phenylalkyl of 7 to 12 carbon atoms, inclusive, with the further proviso that the various substituents are the same or different;
(c) benzhydryl;
(d) benzhydryl substituted by one to 10 alkyl of one to 4 carbon atoms, inclusive, chloro, bromo, iodo, fluoro, nitro, phenalkyl of 7 to 12 carbon atoms, inclusive, with the further proviso that the various substituents are the same or different on each of the aromatic rings;
(e) trityl;
(f) trityl substituted by one to 15 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings.

The introduction of such ether linkages to the hydroxy-containing compounds herein, particularly the benzyl or substituted benzyl ether proceeds by methods known in the art, for example by reaction of the hydroxy-containing compound with the benzyl or substituted benzyl halide (chloride, bromide, or iodide) corresponding to the desired ether. This reaction proceeds in the presence of an appropriate condensing agent (e.g., silver oxide). The mixture is stirred and heated to 50°-80° C. Reaction times of 4 to 20 hr are ordinarily sufficient.

The novel CBA analogs disclosed herein wherein $R_{12}$ is hydrogen produce certain prostacyclin-like pharmacological responses.

Accordingly, the novel formula IV wherein $R_{12}$ is hydrogen are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and as antithrombotic agents as indicated below. The compounds of Formula IV wherein $R_{12}$ is hydrogen are particularly useful in that said compounds possess an improved ratio of platelet aggregation to blood pressure lowering effects as compared to closely related compounds.

(a) Platelet Aggregation Inhibition

The compounds of formula IV wherein $R_{12}$ is hydrogen are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2-4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 μg per ml of whole blood. These compounds, i.e., the compounds of formula IV wherein $R_2$ is hydrogen are useful in the treatment of peripheral vascular dieases, in the same manner as described in U.S. Pat. No. 4,103,026.

(b) Gastric Secretion Reduction

Compounds of Formula IV wherein $R_{12}$ is hydrogen are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 μg to about 20 μg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

Compounds of Formula IV wherein $R_{12}$ is hydrogen are also useful in reducing the undesirable gastrointestinal effects resulting from system administration of the anti-inflammatory prostaglandin synthetase inhibitors, and are useful for that purpse of concomitant administration of said compounds of Formula IV and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula IV compounds are useful, for example, in inducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administrated in any of the ways known in the art to alleviate an inflammatory conditions, for example, in any dosage regimen and by any of the known routes of systemic administration.

(d) Bronchodilation (Anti-asthma)

The compounds of Formula IV wherein $R_{12}$ is hydrogen are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used to 1 to 4 times a day, the exact dose depending on the age, weight, and condition of the patient and on the frequency and route of administration. For the above use Formula IV compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula IV compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When Q is $-COOR_5$, the novel Formula IV compounds so described are used for the purposes described above in the free acid form, in ester form, or in pharmacologically acceptable salt form. When the ester form is used, the ester is any of those within the above definition of $R_5$. However, it is preferred that the ester by alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula IV for the purposes described above are those with pharmacologically acceptable metal cations, ammonia, amine cations, or quaternary ammoniun cations. Illustrative pharmacological acceptable cations which $R_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic, aralipatic amines containing up to and including about 18 carbon atoms, as well as heterocyclic amines, e.g., piperidine, morpholine, pyrrolidine, piperazine, and lower-alkyl derivates thereto, e.g., 1- methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydropholic groups, e.g, mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl) aminomethane, N-phenylethanolamine, N-(p-tert-amylphenyl)-diethanolamine, glactamine, N-methylglycamine, N-methylglucosamine, ephedrine, phenylephrine, epinephrine, procaine, and the like. Further useful amines salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When Q is $-CH_2NL_3L_4$, the Formula IV compounds so described are used for the purposes described in either free base or pharmacologically acceptable acid addition salt form.

The acid addition salts of the 2-decarboxy-2-aminomethyl- or 2-(substituted aminomethyl)-Formula IV compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula IV with the stoichiometric amount of the acid corresponding to the pharmacologically acceptable acid addition salts.

To obtain the optimum combination of biological response specificity, potency, and duration of activity, certain compounds within the scope of this invention are preferred. Preferred compounds of the present invention are the CBA$_2$ analogs, i.e., the copounds of Formula IV wherein the C-5,6 position is unsaturated, and of these compounds those wherein Y is —CH$_2$CH$_2$—, —C≡C— or trans —CH═CH— and/or Q is —COOR$_5$ or —COL$_2$ are preferred especially when R$_5$ is hydrogen, methyl, ethyl, or a pharmacologically acceptable cation such as sodium, and when each of R$_9$ and R$_{10}$ of the L$_2$ substituent moiety is hydrogen. Of these preferred compounds those wherein R$_3$ is hydrogen are more preferred. To further characterize are preferred embodiments of the present invention, compounds of Formula IV wherein

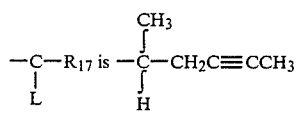

are more preferred particularly when R$_{30}$ and R taken together are —CH$_2$—. Compounds wherein R is methyl are also more particularly preferred also.

Preferred for biological potency are formula IV CBA$_2$ analogs exhibiting the same C-5 isomeric configuration as CBA$_2$ itself. As is apparent from the foregoing as compounds which satisfy more of the above preferences said compounds are more preferred.

The carbacyclin analogs of the present invention as represented by Formula IV are prepared by various procedures which are all generally known in the art. The various charts provided herein are useful in illustrating the preparation of the compounds.

In each of the charts the substituent groups s, L, M, Y, L$_1$, R$_{17}$, Q, R, R$_{30}$, and g have the meanings defined in Formula IV, and R$_{21}$ is a silyl protecting group as defined hereinabove. The group Z$_1$ has the same meaning as Z except Z$_1$ other than —(Ph)—(CH$_2$)$_g$—. The group Q' has the same meaning as Q except Q' is not —COOH.

As indicated hereinabove the hydroxyl groups at positions C-11 and C-15 of the compounds of the present invention may be protected by various groups generally employed in the art and protection of the hydroxyl functions is generally desirable or necessary during the preparation of the compounds. Although any of the various protecting groups described herein may be employed those preferred are tetrahydropyranyl (THP) and tert-butyldimethylsilyl. Particularly, THP is a preferred protecting group during the various reactions required to add the side chains and t-butyldimethylsilyl is a preferred group to employ during separation of the isomers. Of course it may be useful or desirable to utilize protecting groups which may be selectively hydrolyzed.

Also, it will be apparent that in the preparation of the compounds the 5(E) and 5(A) isomers generally may be separated when the C-11 and C-15 hydroxyl groups are either protected or are unprotected. However, it has been found that protection of these hydroxyl groups with, e.g., tert-butyldimethyl silyl often facilitates clean separation of the isomers in high yield. Separation of the 5(E) and 5(Z) isomers is achieved by conventional means, typically column chromatography is employed.

Referring to Chart A wherein there is represented schematically the preparation of 9β-alkylC$_1$-C$_4$ and 6a,9-methano-substituted compounds (Formula A-2) which are novel intermediates useful in preparing the Formula IV compounds and which are regarded as part of the present invention. The enones of Formula A-1 are known in the art or are prepared by procedures known in the art as generally described hereinbelow.

To obtain the 9β-alkylC$_1$-C$_4$ substituted intermediates of Formula A-2 enones of Formula A-1 are treated with lithium dialkyl cuprate in, e.g., diethyl ether. The appropriate lithium dialkyl cuprate is prepared by conventional means, e.g., by reaction of anhydrous copper iodide in diethyl ether with an alkyllithium in diethyl ether. To obtain the 6a,9-methano substituted compounds of Formula A-3 the enones of Formula A-1 are treated with the anion of trimethyloxosulfonium iodide as generally described by E. J. Corey, J. Am. Chem. Soc. 87, 1353 (1965). The anion is conveniently generated by treatment of trimethyloxosulfonium iodide in sodium hydride. Alternatively, the intermediates of Formula A-3 are prepared by treating the corresponding 9β-CH$_2$OH derivative with an excess (e.g., two equivalents) of p-toluenesulfonyl chloride or methanesulfonyl chloride in a tertiary amine base to yield the corresponding tosylate or mesylate derivatives. The tosylate or mesylate derivatives are treated with a base such as potassium tert-butoxide to give the 6a,9-methano intermediates of Formula A-3. To obtain the 9β-CH$_2$OH compounds, compounds of Formula A-1 are subjected to photochemical addition of methanol in a manner analogous to the procedure described by G. L. Bundy, Tetrahedron Lett. 1957 (1975).

The compounds of Formula A-2 and A-3 are utilized to prepare novel compounds of Formula IV wherein D is —C═C(~R$_3$)— and R$_3$ is hydrogen as represented in Chart B. The compounds of Formulas A-2 and A-3 are subjected to a Wittig reaction using an appropriate triphenylphosphorane of Formula B-1 by procedures known in the art, then if desired the hydroxyl protecting groups which are present at at C-11 and C-15 are removed by hydrolysis as generally described hereinabove to give compounds of Formula B-2. The compounds of Formula B-2 are used to prepare the Formula B-3 compounds wherein Q' is the same as Q except it is other than —COOH. The acids of Formula B-2 can be esterified or converted to an amide derivative by conventional means. The Formula B-2 acids or an ester thereof can be reduced to the corresponding alcohol, i.e., Formula B-3 wherein Q' is —CH$_2$OH by standard procedures, e.g., by refluxing with lithium aluminum hydride in an ester solvent. The alcohol thus obtained or a carboxylic acid ester derivative formula B-2 can be oxidized to the corresponding carboxaldehyde which upon treatment with salt of hydroxylamine gives the oxime which is dehydrated to give the nitrile, i.e., the compounds of Formula B-3 wherein Q' is CN. These conversions are all carried out by procedures generally known in the art. See, for example, the aforementioned British specifications which describe the synthesis of various carbacyclin compounds, and in particular G.B. 2,013,661. The amide thus obtained can be reduced to the corresponding amines, i.e., compounds of Formula B-3 wherein Q' is —CH₂L₃L₄ by using, e.g., lithium aluminum hydride. See U.S. Pat. No. 4,073,808. Of course during the conversion of the Formula B-2 acids to the various other C-1 position derivatives as represented by Formula B-3, the C-11 and C-15 hydroxyl groups are protected as described herein which groups can ultimately be deprotected by hydrolysis. The 5(E) and 5(Z) isomers can be separated using either the compound of Formula B-2 or Formula B-3.

The compounds of Formula IV wherein D is —CH=C(~R₃) wherein R₃ is hydrogen and wherein Z is —(Ph)—(CH₂)$_q$— are prepared as follows reference being made to Chart F. The ketones of Formulas A-2 and A-3 are reduced by conventional means using, for example, a borohydride reducing agent such as sodium, potassium or lithium borohydride, to the corresponding alcohol. The alcohol is converted to a sulfate derivative, typically a methanesulfonate or toluenesulfonate by treatment with methanesulfonyl chloride or toluenesulfonyl chloride in the presence of a tertiary amine such as triethylamine. The sulfonate derivative is treated with sodium, lithium or potassium thiophenoxide to give the compounds of Formula F-1. The thiophenoxide is preferably prepared by reacting equal molar amounts of thiophenol and a base such as potassium tertiary butoxide just prior to reaction with the sulfonate. The compounds of Formula F-1 are oxidized to the corresponding phenylsulfonate using, e.g., m-chloroperbenzoic acid then treated with a strong base such as n-butyllithium to generate the corresponding anion. The anion is treated with an aldehyde of Formula F-2 and the resulting adduct is treated with acetic anhydride to give compounds of Formula F-3. The compounds of Formula F-3 are treated with sodium amalgam by procedures analogous to those described by P. J. Kocienski, et al., "Scope and Stereochemistry of an Olefin Synthesis from β-Hydroxylsulphones", JCS Perkin I, 829–834 (1978) to give the olefins of Formula F-4. The compounds of Formula F-4 are used to prepare the products of Formula F-5. The various hydroxyl groups are protected in such a manner to permit selected hydrolysis to give ultimately the deprotected products of Formula F-5. The R₂₁ silyl protecting group is conveniently removed via fluoride mediated hydrolysis using, e.g., tetrabutyl ammonium fluoride to give the C-1 position alcohol of Formula F-5 which is oxidized, using, e.g., Jones reagent, to the corresponding carboxylic acid which in turn can be converted to the corresponding esters and amides. Also, the amides can be reduced to the amines of Formula F-5, i.e., compounds wherein Q is —CH₂L₃L₄, and the alcohol or the carboxylic acid esters can be oxidized to the carboxaldehyde then converted to the nitrile via the oxime. The general procedures are the same as those described hereinabove in connection with the preparation of compounds of Formula B-3. The 5(E) and 5(Z) isomers can be separated conveniently using the alcohol corresponding to Formula F-4 and the C-11 and C-15 hydroxyl protecting groups which may be present are removed by mild acid hydrolysis using, e.g., mixtures of water, tetrahydrofuran and acetic acid.

The compounds of Formula F-2 are prepared using known bis-acids of the formula

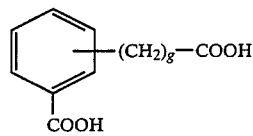

wherein g is zero, one, 2 or 3, which are reduced to the corresponding diol by conventional procedures, e.g., by using lithium aluminum hydride. About equal molar amounts of the diol and a silylating reagent of R₂₁ are combined thereby preferentially silylating the alkanol hydroxyl although some di-silylated compound is produced. The mono-silylated compounds of the formula

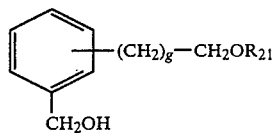

are oxidized to the aldehydes of Formula F-2 by conventional means, e.g., using manganese dioxide. See. U.S. Pat. No. 4,306,075.

The compounds of Formula IV wherein D is —CH=C(~R₃) and R₃ is fluoro are prepared by reacting compounds of Formula A-2 and A-3 from Chart A hereof with a sulfoxime of the formula G-1 as depicted in Chart G by the general procedures described in U.S. Pat. No. 4,238,414 at column 30, lines 36 to 62. The compounds of Formula G-2 are then selectively hydrolyzed to the primary alcohol using, e.g., tetra-n-butylammonium fluoride. The alcohols thus obtained can be oxidized to the corresponding C-1 position carboxylic acids, esters, amides, amines and nitriles of Formula G-3 by the same general procedures described hereinabove in reference to the preparation of compounds of Formula F-5 in Chart F. The 5(E) and 5(Z) isomers can be separated conveniently using the primary alcohol corresponding to Formula G-2, and the C-11 and C-15 hydroxyl protecting groups are removed by mild acid hydrolysis.

The sulfoxime of Formula G-1 are prepared by treating a compound of the formula

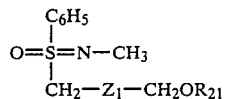

wherein Z₁ R₂₁ have the meanings defined hereinabove, which compounds are known in the art (See U.S. Pat. No. 4,238,414) or are prepared by procedures generally known in the art with a strong base such as n-butyllithium in hexane to generate the anion which is treated with a fluorine source a preferred fluorine source being perchloryl fluoride, i.e., FClO₃.

The compounds of Formula IV can also be prepared utilizing compounds of the following Formula PX. In Formula PX, L₅₀ has the same meaning as L only R₁₂ is other than hydrogen; and R₁₃ is a protecting group as defined hereinabove.

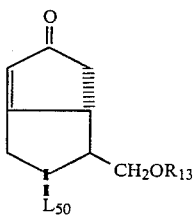

Formula PX

In referring to Chart A when the Compounds of Formula PX are substituted for and reacted in the manner analogous to that described for compounds of Formula A-1 one obtains compounds of the following Formula PX(a) wherein R and $R_{30}$ have the meanings defined in Formula IV, and $R_{13}$ and $L_{50}$ have the meanings defined in Formula PX.

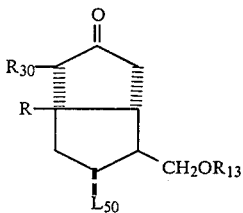

Formula PX(a)

When the compounds of Formulas PX(a) are substituted for and treated in a manner analogous to that described for the compounds of Formulas A-2 and A-3 as set forth in Chart B compounds of the following Formula PX(f) are obtained:

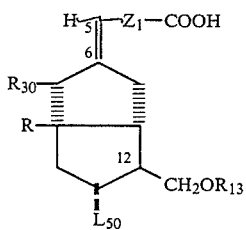

Formula PX(f)

wherein $R_{13}$, $Z_1$ and $L_{50}$ have the meanings defined hereinbefore and R and $R_{30}$ have the meanings defined in Formula IV. The compounds of Formula PX(f) can be converted to compounds of Formula PX(g) when treated in manners analogous to those described for the compounds of Formula B-2 in Chart B.

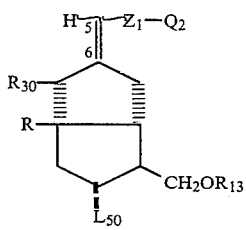

Formula PX(g)

In Formula PX(g) the various substituent groups R, $R_{30}$, $L_{50}$, $R_{13}$ and $Z_1$ have the meanings defined in Formula PX(f) and $Q_2$ is the same as Q only $Q_2$ is not —COOH.

When the compounds of Formulas PX(a) are substituted for the compounds of Formulas A-2 and A-3 in Chart F and the general procedures described with respect to Chart F are followed, or when the compounds of Formulas PX(a) are substituted for the compounds of Formulas A-2 and A-3 in Chart G and the general procedures described in Chart G are followed intermediates of the following respective Formulas PX(l) and PX(m) are obtained wherein g, Q, $R_{13}$, $L_{50}$, R and $R_{30}$ have the meanings defined hereinbefore

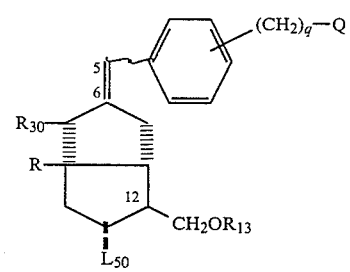

Formula PX(l)

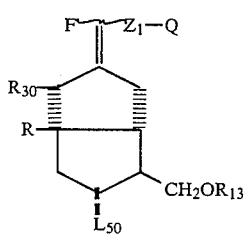

Formula PX(m)

The intermediates of Formulas PX(f), PX(g), PX(l) and PX(m) are utilized in preparing the $CBA_2$ compounds of Formula A-1 (Chart A). Initially the intermediates of Formulas PX(f), (g), (l) and (m) are hydrolyzed to remove the $R_{13}$ protecting group thus giving the primary alcohol derivatives which are oxidized to the corresponding aldehyde by conventional procedures, e.g., under the conditions of a Collins reaction. To prepare compounds of Formula A-1 one utilizes aldehydes of the following general Formula MX which are obtained by oxidation of the corresponding C-12 position substituted alcohol by conventional procedures. The alcohols are known in the art or are readily prepared by procedures known in the art.

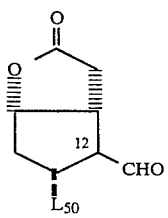

Formula MX

In the above Formula MX, $L_{50}$ has the meaning defined in Formula PX above.

The "C-12 aldehydes" corresponding to the intermediates of Formulas PX(f), PX(g), PX(l) and PX(m) and the aldehydes of Formula MX are then treated as described hereinbelow, wherein for purposes of convenience only the chemical transformations which occur at the "C-12 position" of said compounds are depicted.

The "C-12" aldehydes are subject to a Wittig reaction with an alkyl phosphonate derivative of the formula

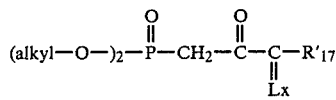

which is obtained by addition of the anion of dialkylmethylphosphonate, i.e.,

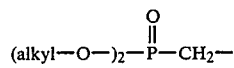

with an ester of the formula

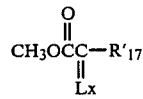

by procedures known in the art. $R'_{17}$ and $L_x$ have the same meanings as $R_{17}$ and $L_1$ except

is other than $-C_pH_{2p}CH=CH_2$. There results compounds wherein the "C-12 position" is substituted with

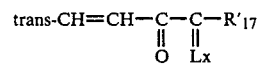

the ketone of which is reduced to the various M groups defined hereinabove to give the corresponding compounds wherein the "C-12 position" is substituted with

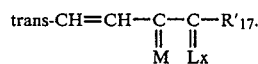

These trans-vinyl derivatives can be hydrogenated to give the corresponding compounds wherein the "C-12 position" is substituted with

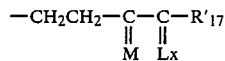

or can be halogenated followed by tetradehydrohalogenation to give the corresponding compounds wherein the "C-12 position" is substituted with

and upon hydrogenation with a Lindlar catalyst gives the cis-vinyl derivatives, i.e., compounds wherein the "C-12 position" is substituted with

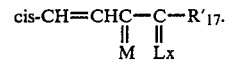

Compounds corresponding to those of Formulas MX or PX(f), (g), (l) and (m) wherein the "C-12 position" is substituted with

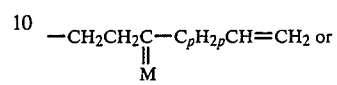

can also be prepared by treating the appropriate "C-12" aldehyde compound with an alkylphosphonate depicted above only wherein

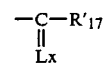

is $-C_pH_{2p}CH=CH_2$ or

to give the corresponding compounds wherein the "C-12 position" is substituted with

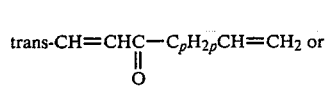

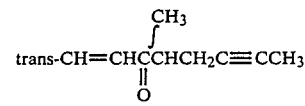

the trans-vinyl group of which is reduced, e.g., by dissolving metal reduction followed by reduction of the ketone to the various M groups defined hereinabove.

Additionally, treatment of the "C-12" aldehydes with a phosphine of the formula $(alkyl)_3P=CHCHO$ under the conditions of a Wittig reaction gives the corresponding compounds wherein the "C-12" position is substituted with trans—$CH=CHCHO$ which can be reduced to give the corresponding compound wherein the "C-12 position" is substituted with $-CH_2CH_2-CHO$. Also the compounds corresponding to the Formula MX or Formulas PX(f), (g), (l) or (m) only wherein the "C-12 position" is substituted with trans—$CH=CHCHO$ can be reduced to the corresponding alcohol, i.e., trans—$CH=CHCH_2OH$ then hydrogenated to give compounds wherein the "C-12 position" is substituted with —$CH_2CH_2CH_2OH$. Or, the trans-vinyl alcohol can be halogenated then tetradehydrohalogenated to give the corresponding ethinyl, i.e., compounds wherein the "C-12 position" is substituted with —$C\equiv CCH_2OH$, which upon hydrogenation with a Lindlar catalyst gives the cis-vinyl alcohol compounds. The thus obtained alcohols, i.e., the compounds corresponding to those of Formulas MX or PX(f), PX(g), PX(l) and PX(m) only wherein the "C-12 position" is substituted with trans—CH=CHCH₂OH, —CH₂CH₂CH₂OH, —C≡CCH₂OH or cis—CH=CHCH₂OH can then be oxidized to the aldehyde to give the corresponding compounds wherein the terminal primary alcohol contained in the "C-12" substituent is —CHO. The aldehydes are then treated with a Grignard reagent of the formula haloMgC$_p$H$_{2p}$CH=CH₂ or an alkyllithium of the formula LiC$_p$H$_{2p}$CH=CH₂, or an acetylide anion of the formula —C≡CC$_p$H$_{2p}$CH₃ or an alkylphosphonate depicted hereinabove to give compounds corresponding to those of Formulas MX or PX(f), (l), (m) and (g) only wherein the "C-12 position" is substituted with

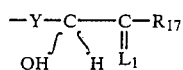

wherein Y, L₁ and R₁₇ have the meanings defined hereinabove. These thus obtained alcohol derivatives can be oxidized to the ketone and treated with methyl lithium or a methyl Grignard to give the corresponding compounds wherein the "C-12 position" is substituted with

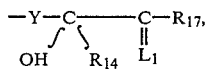

wherein R₁₄ is methyl.

Upon completion of the above-described "C-12 position" transformations with respect to the compounds of Formula MX the resulting lactone derivatives are converted to the compounds of Formula A-1 via lactol and diketone phosphonate derivatives in a manner analogous to that described in U.S. Pat. No. 4,306,075 in reference to Chart A thereof.

The CBA₁ compounds of Formula IV, i.e., compounds of Formula IV wherein D is —CH₂CH₂— are prepared by reducing the compounds of Formulas PX(f), PX(g) and PX(l) to the corresponding derivatives wherein the carbon atoms at positions C-5 and C-6 are saturated. This reduction is carried out by procedures generally known in the art, such as the general methods described in British Published application 2,017,699. For example, the reduction may be achieved by a standard hydrogenation in the presence of a catalyst such as palladium on charcoal or platinum dioxide in a lower alcohol such as ethanol or methanol. The resulting 5,6-dihydro intermediates are then utilized to prepare the CBA₁ compounds of Formula IV by the same general procedures described hereinabove in connection with the conversion of compounds of Formulas PX(f), PX(g) and PX(l) to CBA₂ compounds of Formula IV.

A preferred method of preparing the CBA₁ compounds of Formula IV wherein Z is trans—CH₂CH=CH— is to utilize the appropriate intermediates of Formulas PX(m) and PX(g) wherein Z₁ is —CH₂—(CH₂)$_f$—C(R₄)₂— wherein f is one and R₄ is hydrogen and wherein Q is a carboxylic acid ester, preferably the methyl ester which derivatives are referred to herein as the butanoic acid esters. The butanoic acid ester derivatives are treated with a lithium amide base and phenylselenyl chloride to give the corresponds α-phenylselenyl derivatives which are reduced by, e.g., general procedures described in U.K. application GB2,017,699 to give the 5,6-dihydro intermediates. The 5,6-dihydro intermediates are dehydrophenylselenized by treatment with hydrogen peroxide to give intermediates corresponding to Formulas PX(g) to PX(k) wherein Z₁ is —CH₂CH=CH₂, Q² is a carboxylic acid ester and the carbon atoms at positions 5 and 6 are saturated, which intermediates can be converted to the corresponding derivatives wherein the terminal C-1 position corresponds to Q as defined herein by the general procedures described hereinabove in connection with the preparation of compounds of Formula B-3 in Chart B. These 5,6-dihydro intermediates are then converted to the CBA₁ compounds of Formula IV wherein Z is —CH₂CH=CH— by treatment in a manner analogous to that described hereinabove in connection with the conversion of Formulas PX(f)–PX(r) to CBA₂ compounds of Formula IV.

When the alkyl ester has been obtained and an acid is desired, saponification procedures, as known in the art for PGF-type compounds are employed.

When an acid has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similary, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acd reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield and purity of product.

With regard to the preparation of the phenyl, particularly p-substituted phenyl esters disclosed herein (i.e., Q is —COOR₅ and R₅ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift 2,535,693, and Derwent Farmdoc No. 16828X.

The phthalidyl esters are obtained by treating the corresponding acid with a phthalidyl halide such as the bromide in, e.g., dimethyl-formamide in the presence of an amine base. The phosphoranyl esters are obtained by treating the corresponding acid with a 1-halo derivative, e.g., the 1-chloro derivative of 3-(5,5-di(hydroxymethyl)-1,3,2-dioxaphosphorinan-2-yl)-2-oxopropan-1-yl P-oxide and 3-(5,5-dimethyl-1,3,2-dioxaphosphorinan-2-yl)-2-oxopropan-1-yl P-oxide in, e.g., acetonitrile in the presence of an organic amine.

Carboxyamides (Q is —COL$_2$) are prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The prepared method by which the present amido and cycloamido derivatives of the acids are prepared is, first, by transformation of such free acids to corresponding mixed acid anhydrides. By this procedure, the carbacyclin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at $-10°$ C. to $20°$ C.

Thereafter, the mixed anhydride is converted to the corresponding amido or cycloamido derivatives by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete.

Thereafter, the novel amido or cycloamido derivative is recovered from the reaction mixture by conventional techniques.

The carbonylamido and sulfonylamido derivative of the presently disclosed carbacyclin compounds are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure carbacyclin sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temperatures at or about $0°$ C. are employed.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation if inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

EXAMPLE 1

(a)

6β-(Benzyloxymethyl)-7α-(tetrahydropyran-2-yloxy)-1β-(methyl)-bicyclo[3.3.0]octan-3-one To a mixture of 3.46 g of copper iodide in 180 ml of diethyl ether, cooled to −10° C. in a carbon tetrachloride-dry ice bath, is added dropwise 28.0 ml (36.42 mmoles) of methyl lithium over a 5 minute period and stirring is continued for 20 minutes at −20° to −23° C., after which 6β-(benzyloxy)methyl]-7α-(tetrahydropyran-2-yloxy)bicyclo[3.3.0]octen-3-one in 98 ml of diethyl ether is added dropwise over about one hour. Stirring is continued at −20° C. for about 2 hours then under a nitrogen atmosphere the mixture is combined with 100 ml of 0.5M ammonium chloride, cooled with stirring. The organic layer is separated, and the aqueous layer is extracted with 500 ml of ether, dried and the combined organic extracts are concentrated on a rotary evaporator to give 2.3 g of crude material which is chromatographed with silica gel using ethyl acetate-Skelly "B" for packing and eluting to give the purified title product as a colorless oil.

TLC: Ethyl acetate-Skelly "B" (1:2 ($R_f$ 0.48.

(b)

12β-(Benzyloxymethyl)-9β-methyl-13,14,15,16,17,18,19,20-octanor-6a-carba-prostaglandin $I_2$, 11-tetrahydropyranyl ether Sodium hydride (6.93 g, 60% oil dispersion, 173.1 mmol, 11.5 eq) is stirred in 7 ml of dry hexane, allowed to settle and the supernatant carefully drawn off with pipette. After repeating above procedure using 10 ml of hexane, 132 ml of dimethylsulfoxide is added and the mixture heated in oil bath at 75° C. under nitrogen for 1.3 hours. The dimethylsulfoxide anion is cooled to about 10° C., treated portionwise with solid 4-carboxybutyl triphenylphosphonium bromide (38.03 g, 85.8 mmol, 5.7 eq) over a short period of time (1 to 2 minutes). The contents are stirred at ambient temperature for 1.2 hours additionally, then treated dropwise over a 5 minute period with the product of 1(a) above (5.39 g, 15.06 mmol) in 46 ml of dimethylsulfoxide at room temperature. The reaction mixture is kept in oil bath at 45° C. for about 43 hours, cooled in ice bath, poured into 350 ml of 2N potassium bisulfate solution containing 150 ml of ice and extracted with ether three times. The combined ether extracts are dried over anhydrous sodium sulfate and concentrated at reduced pressure to yield 17.8 g of crude material. Following chromatography with 500 g of silica gel packed and eluted with acetone-Skelly "B" (1:4) plus 0.25% acetic acid, 5.46 g (82%) of the title product is isolated as a 5E and 5Z mixture.

TLC: Acetone-Skelly "B"-acetic acid (20:80:.25) $R_f$ 0.21.

(c)

12β-Hydroxymethyl-9β-methyl-13,14,15,16,17,18,19,20-octanor-6a-carba prostaglandin $I_2$, 11-tetrahydropyranyl ether Liquid ammonia (100 ml) is distilled into a solution of the product of 1(b) above (5.46 g, 12.34 mmol) in 100 ml of tetrahydrofuran and 2.0 ml of t-butyl-alcohol at −50° C. utilizing a dry ice-acetone trap. The temperature is maintained at about −40° C. while freshly scraped lithium wire (4″) is added in small pieces portionwise. After 15 minutes an additional 2″ of lithium wire is added causing the gray suspension to change to blue. After an additional 30 minutes solid NH$_4$Cl is added to quench excess lithium and a strong nitrogen stream is swept through flask to expel the excess ammonia. To the solid residue is added 100 ml of saturated ammonium chloride solution plus 100 ml of 2W potassium bisulfate solution. The contents are extracted with ethyl acetate two times, the combined ethyl acetate extracts washed with saturated brine (1×75 ml) and dried over anhydrous sodium sulfate. Concentration in vacuo leads to 4.54 q of colorless oil. Separation of the 5Z (42%) and 5E (39%) isomers of the title compound is achieved by HPLC (2-'C' and 3-'B' prepacked Merck columns in series) using ethyl acetate-Skelly "B" 91:2) containing 0.25% acetic acid.

TLC: Ethyl acetate-Skelly "B" (1:1) with 0.25% acetic acid $R_f$ 5Z 0.26, $R_f$ 5E 0.20.

(d)

(5E)-12β-Hydroxymethyl-9β-methyl-13,14,15,16,17,18,19,20-octanor-6a-carba-prostaglandin $I_2$ methyl ester, 11-tetrahydropyranyl ether To a stirred solution of the 5E isomer of 1(c) above (1.72 g, 4.87 mmol) in 25 ml of acetonitrile at room temperature is added diisopropylethylamine (1.88 g, 14.61 mmol, 3 eq) at once followed by methyl iodide (3.46 g, 24.36 mmol, 5 eq) in like manner. After 21 hours at room temperature the reaction mixture is diluted with a sufficient amount of ether, washed successively with saturated brine (1×50 ml), 10% sodium thiosulfite (1×20 ml), and saturated brine (1×25 ml). The combined aqueous washings are extracted with ether (1×100 ml) and the combined organic extracts dried over anhydrous sodium sulfate. Concentration in vacuo provides 1.68 g (94%) of the title product as a dark brown oil.

TLC: Ethyl acetate-Skelly "B" (1:1) with 1% acetic-acid $R_f$ 0.44.

(e)

(5E)-12β-Formyl-9β-methyl-13,14,15,16,17,18,19,20-octanor-6a-carba-prostaglandin $I_2$ methyl ester, 11-tetrahydropyranyl ether To a suspension of dry chromium trioxide (0.793 g, 7.93 mmol, 6 eq) in 13 ml of methylene chloride at room temperature is added pyridine (1.25 g, 15.84 mmol, 12 eq) dropwise followed by 1 ml methylene chloride rinse. After 1.3 hours of stirring at ambient temperature the reaction mixture is cooled in an ice bath while the product of 1(d) above (0.485 g, 1.32 mmol) in 6 ml of methylene chloride is added dropwise over a 5 minute period. The cooling bath is removed, 5 ml of additional methylene chloride is added and the contents are stirred for 45 minutes at ambient temperature. Subsequently, the mixture is diluted with ether, celite and stirred at room temperature for about 30 minutes. The contents are filtered through a pad of celite and the filtrate concentrated at reduced pressure to obtain 475 mg of crude product as a brown oil. Purification, effected with a 50 g silica gel column packed and eluted with ethyl acetate-Skelly "B" (1:4), gives 370 mg (76%) of pure title compound.

TLC: Ethyl acetate-Skelly "B" (1:4) $R_f$ 0.32.

EXAMPLE 2

(a) 1-Bromo-2-butyne

To a stirred solution of 2-butyne-1-ol (10.0 g, 0.143 mol) in 30 ml of ether at 0° C. is added pyridine (4.84 g, 0.06 mol, 0.43 eq) at once followed by careful dropwise addition of phosphorous tribromide (26.3 g, 0.097 mol, 0.68 eq) over a 30 minute period. An additional 10 ml of ether was added to facilitate stirring and the contents warmed to reflux for 2 hours. The reaction mixture is cooled in ice bath, treated cautiously with 70 ml of ice water and extracted with ether (2×150 ml). The combined ether extracts are washed with saturated brine (2×25 ml), the combined aqueous washings extracted with ether (1×50 ml) and the combined organic extracts dried over anhydrous sodium sulfate. The filtrate is concentrated on a rotary evaporator while keeping the water bath temperature less than 10° C. Twice the contents are diluted with 100 ml of pentane and reconcentrated as before. The heterogenous looking oil is dissolved in 300 ml of pentane, dried over anhydrous magnesium sulfate and reconcentrated as before to obtain 11.0 g (58%) of 1-bromo-2-butyne.

(b) 2-Methyl-4-hexynoic acid

Diisopropylamine (26.0 g, 0.257 mmol, 3.1 eq) in 130 ml of tetrahydrofuran initially at −50° C. is treated dropwise with n-butyllithium (98.8 ml, 1.6 M, 0.158 mol, 1.9 eq) over an 8 minute period while allowing the temperature to rise to −25° C. After 5 minutes longer at −20° C., the reaction mixture is treated dropwise with a mixture of hexamethylphosphoramide (17.8 g, 0.099 mol, 1,2 eq) and propionic acid (6.14 g, 0.083 mol, 1.0 eq) over a 7 minute period while the temperature rises to 0° C. Following addition the reaction mixture is warmed to room temperature and maintained there for 35 minutes. The contents are then cooled to 0° C. in an ice bath, treated dropwise over a 12 minute period with 1-bromo-2-butyne (11.0 g, 0.083 mol, 1.0 eq) in 8 ml of tetrahydrofuran. The temperature, which rises to 16° C. during addition, is allowed to warm to room temperature thereafter where it is maintained for 2 hours. The contents are carefully poured into 300 ml of 10% HCl with stirring (exothermic) followed by 500 ml of ether-pentane (1:1). The organic layer is separated and the aqueous phase extracted 2 more times with etherpentane (1:1) giving 1800 ml of total extract volume. The combined extracts are washed with water 2×60 ml) and the combined organic extracts are dried over anhydrous sodium sulfate, magnesium sulfate and concentrated at reduced pressure to provide 11.1 g (over theory) of 2-methyl-4-hexynoic acid which is converted to the methyl ester by treatment with methyl iodide.

(c) 3-Methyl-2-oxo-hept-5-yne phosphonic acid dimethyl ester

A solution of dimethyl methylphosphonate (22.47 g, 181.24 mmol) in 260 ml of tetrahydrofuran is cooled to −78° C. and treated dropwise with n-butyllithium (113 ml, 181.24 mmol), 1.6 M in hexane) over a 25-minute period. The mixture is stirred an additional 30 minutes at −78° C., then treated dropwise with 2-methyl-4-hexynoic acid methyl ester (7.25 g, 51.78 mmols) in 65 ml of tetrahydrofuran over a period of 10 minutes. The contents are stirred for another 3 hours at −78° C. and then 17 hours at ambient temperature. The reaction mixture is cooled to 8° C., treated with 14 ml of acetic acid, stirred at ambient temperature for 30 minutes, then concentrated in vacuo. The residue is treated with 100 ml of saturated brine and 100 ml of ice water to form a slurry and extracted 3 times with ether (1400 ml total) and once with 250 ml of ethyl acetate-ether (1:1). The combined organic extracts are washed with saturated brine (2×75 ml), the combined aqueous washings extracted with ethyl acetate-ether (1:1, 1×100 ml) and dried over anhydrous sodium sulfate, and concentrated at reduced pressure. Vacuum distillation gives 10.21 g of the title product, m.p. 121°–125° C., 0.15 mmHg.

EXAMPLE 3

(a) (5E)-9$\beta$-Methyl-15-keto-16(R,S)-16-methyl-18,19-tetradehydro-6a-carba-prostaglandin I$_2$, methyl ester, 11-tetrahydropyranyl ether Thallium ethoxide (0.634 g, 2.55 mmol, 1.3 eq) in 10 ml of benzene at 6° C. is treated with 3-methyl-2-oxohept-5-yne phosphonic acid dimethyl ester (0.613 g, 2.64 mmol, 1.35 eq) in 2.5 ml of benzene. After stirring for 50 minutes at 6° to 10° C., (5E)-12$\beta$-formyl-9$\beta$-methyl-13,14,15,16,17,18,19,20-octanor-6a-carba-prostglandin I$_2$ methyl ester, 11-tetrahydropyranyl ether (0.715 g, 1.96 mmol) in 5 ml of benzene is added at once to mixture at 6° C. After stirring one hour longer at ambient temperature, the reaction mixture is again cooled to 6° C., quenched with 0.5 ml of acetic acid followed by addition of aqueous potassium iodide to precipitate the thallium as a yellow salt. The contents are diluted with ether, stirred at room temperature and filtered through a pad of celite. The organic layer is washed successively with ice water (1×50 ml), saturated sodium bicarbonate (1×75 ml), saturated brine (1×50 ml) and all aqueous washings extracted with ether (1×75 ml). The combined organic extracts are dried over anhydrous sodium sulfate and concentrated in vacuo to obtain 1.25 g of crude product as a yellow oil. Chromatography with 100 g of silica gel using ethyl acetate-Skelly "B" (1:8) for packing and (1:6) for eluting, gives 744 mg (81%) of the title compound.

TLC: Ethyl acetate-Skelly "B" (1:9) $R_f$ 0.11.

(b) (5E)-9$\beta$-Methyl-15(R,S)-16-methyl-18,19-tetradehydro-6a-carba-prostaglandin I$_2$, methyl ester, 11-tetrahydropyranyl ether To a solution of 0.24 g (0.510 mmole) of (5E)-9$\beta$-methyl-15-keto-16(R,S)-16-methyl-18,19-tetradehydro-6a-5Z-carba-prostaglandin I$_2$, methyl ester, 11-tetrahydropyranyl ether in 6 ml of methanol, cooled to −25° C., is added 0.027 g (0.71 mmole) of sodium borohydride in about 1 ml of methanol and the mixture is stirred at −25° to −20° C. then at −20° to −15° C. for about 30 minutes after which an additional 0.027 g (0.71 mmole) then another 0.015 g (0.39 mmole) of sodium borohydride is added with continued stirring. After about 20 minutes the mixture is treated with 7 ml of 2N potassium bisulfate solution and ice water then extracted with ethyl acetate. The organic extract is washed (2×20 ml) with saturated brine, and the aqueous washings are extracted with ethyl acetate. The combined organic extracts are dried over anhydrous sodium sulfate, concentrated in vacuo, and the residue chromatographed on silica gel eluting with ethyl acetate-Skelly "B" to give the title product as a colorless oil.

TLC: Ethyl acetate-Skelly "B" (1:4) $R_f$ 0.15, $R_f$ 0.11.

(c) (5E)-9β-Methyl-15(R) and 15(S)-16(R,S)-16-methyl-18,19-tetradehydro-6a-carba-prostaglandin I$_2$, methyl esters Acid hydrolysis of the product of 3(b) above (0.823 g, 1.74 mmol) is accomplished by stirring with 16.5 ml of acetic acid-water-tetrahydrofuran (20:10:3) at room temperature for 7 hours. The contents are cooled in ice bath, treated with solid sodium bicarbonate plus ice and extracted with ethyl acetate two times (450 ml total volume). The combined organic extracts are washed with 5% sodium bicarbonate (1×25 ml), saturated brine (1×25 ml) and the aqueous washings extracted with ethyl acetate (1×50 ml). The combined organic extracts are dried over anhydrous sodium sulfate and concentrated at reduced pressure to give 771 mg crude diol. LPLC chromatography using a prepacked Merck "B" column and ethyl acetate-Skelly "B"(1:2) 1 l; then (2:3) resolves the 15(R) and 15(S) isomers of the title product.

TLC: Ethyl acetate-Skelly "B" (1:1) R$_f$, 15(R), 0.28; R$_f$, 15(S), 0.18. Acetone-methylene chloride (1:4) R$_f$, 15(R), 0.39; R$_f$, 15(S), 0.18.

IR (neat, cm$^{-1}$): 15(R) and 15(S) identical; 3410 (s, broad), 2950 (s), 1860 (w,sh), 1740 (s), 1715 (sh), 1450 (m), 1430 (m), 1370 (w), 1250 (w), 1170 (w), 1070 (w), 1010 (w), 970 (m).

NMR (CDCl$_3$, δ): 15(R), 5.58 (m, 2H), 5.35–5.00 (m, 1H), 4.53–3.55 (m, 2H), 3.65 (s, 3H), 2.80–1.20 (m, 22H), 1.05 (s, 3H), 1.00 (d, 3H, 7 Hz). 15(S), 5.48 (m, 2H), 5.34–4.94 (m, 1H), 4.16–3.50 (m, 2H), 3.66 (s, 3H), 3.23 (s, 2H), 2.50–1.15 (m, 20H), 1.06 (s, 3H), 0.96 (d, 3H, 7 Hz).

Mass Spectrum: Calculated for C$_{30}$H$_{52}$O$_4$Si$_2$: 532.3404. Found: 15(R), 532.3396; 15(S), 532.3406.

(d) (5E)-9β-Methyl-15(R) and 15(S)-16(R,S)-16-methyl-18,19-tetradehydro-6a-carba-prostaglandin I$_2$ Base hydrolysis of the 15(S) isomer of 3(c) above (0.324 g, 0.834 mmol) in 12 ml of methanol at room temperature is achieved by adding potassium hydroxide (1.4 ml, 3N, 4.2 mmol, 5 eq) at once. After 7.5 hours the reaction mixture is cooled to 0° to 5° C. in ice bath, treated with 13 ml of 2N potassium bisulfate plus 20 ml of saturated brine. The contents are extracted with ethyl acetate 2 times, the combined organic extracts washed with saturated brine (1×25 ml), dried over anhydrous sodium sulfate and concentrated in vacuo. Chromatography with 19 g of CC-4 acid washed silica gel using ethyl acetate-Skelly "B" (1:2) for packing and eluting gives 261 mg (84%) of the title products.

The 15(S) compound is characterized as follows:

TLC: Ethyl acetate-Skelly "B" (1:1) with 1% acetic acid R$_f$ 0.12.

IR (neat, cm$^{-1}$): 3330 (s, broad), 2900 (s), 2650 (broad shoulder), 1700 (s), 1450 (m), 1370 (w), 1240 (w), 1130 (w), 1060 (w), 1000 (w), 970 (m).

NMR (CDCl$_3$, δ): 5.95 (s, 3H), 5.43 (s, 2H), 5.26–4.84 (m, 2H), 4.20–3.45 (m, 2H), 2.43–1.08 (m, 20H), 1.05 (s, 3H), 1.08–0.51 (m 3H).

Mass Spectrum: Calculated for C$_{32}$H$_{58}$O$_4$Si$_3$: 590.3643. Found: 590.3633.

The 15(R) compound is similarly prepared and is characterized as follows:

TLC: Ethyl acetate:Skelly "B" (1:1) with 1% acetic acid, R$_f$ 0.24.

NMR (CDCl$_3$, δ): 5.60 (s, 6H), 5.33–4.94 (m, 1H), 4.27–3.60 (m, 2H), 2.78–1.20 (m, 20H), 1.07 (s, 3H), 1.20–0.70 (m, 3H).

EXAMPLE 4

(a) When in the procedure of Example 1(d) the (5Z) isomer of 12β-hydroxymethyl-9β-methyl-13,14,15,16,17,18,19,20-octanor-6a-carba-prostaglandin I$_2$, 11-tetrahydropyranyl ether is substituted for the (5E) isomer one obtains (5Z)-12β-hydroxymethyl-9β-methyl-13,14,15,16,17,18,19,20-octanor-6A-carba-prostaglandin I$_2$ methyl ester, 11-tetrahydropyranyl ether which is converted to the corresponding 12β formyl derivative by the procedure of Example 1(e).

(b) When in the procedure of Example 3(a) (5Z)-12β-formyl-9β-methyl-13,14,15,16,17,18,19,20-octanor-6a-carba-prostaglandin I$_2$ methyl ester, 11-tetrahydropyranyl ether is substituted for the (5E) isomer and the procedure of Example 3(a) through 3(c) is followed one obtains (5Z)-9β-methyl-15(S)and 15(R)-16(R,S)-16-methyl-18,19-tetradehydro-6a-carba-prostaglandin I$_2$, methyl esters (TLC: ethyl acetatecyclo hexane; 15(S) compound, R$_f$0.27; 15(R) compound, R$_f$0.37) which are converted to the correponding C-1 carboxylic acids by the procedure of Example 3(d). (5Z)-9β-methyl-15(S)-16(R,S)-16-methyl-18,19-tetradehydro-6a-carba-prostaglandin I$_2$ is characterized as follows:

NMR (CDCl$_3$, δ): 6.6 (s, 3H); 5.5 (s, 2H); 5.2 (m, 1H); 4.1–3.6 (m,2H), 1.8 (s, 3H); 1.05 (s, 3H); 0.95 (d, 3H).

IR (thin film): 3365 (OH), 2602 (COOH), 1709 (C=O), 1435, 1432, 1411, 1374, 13331, 1296, 1244, 1205, 1175, 1152, 1119, 1098, 1073, 1044, 1008, 971 cm$^{-1}$.

The corresponding 15(R)compound is characterized as follows:

NMR (CDCl$_3$, δ): 5.7 (m, 5H); 5.2 (m, 1H); 4.3–3.65 (m, 2H); 1.75 (s, 3H); 1.05 (s, 3H); 0.95 (d, 3H).

IR (thin film): 3368 (OH), 2649 (COOH), 1710 (C=O), 1452, 1432, 1411, 1375, 1349, 1335, 1310, 1293, 1247, 1203, 1172, 1151, 1117, 1102, 1072, 1042, 1009, 972 cm$^{-1}$.

EXAMPLE 5

(a) When in the procedure of Example 1(b) 6β-(benzyloxymethyl)-8a-(tetrahydropyran-2-yloxy)-tricyclo[4.3.1]nonan-4-one, which is prepared from 6β-(benzyloxymethyl)-7a-(tetrahydropyran-2-yloxy)bicyclo[3.3.0]octen-3-one in a manner analogous to that described in Example 29 U.S. Pat. No. 4,306,075, is substituted for 6β-(benzyloxymethyl)-7β-(tetrahydropyran-2-yloxy)-1β-(methyl)bicyclo[3.3.0]octan-3-one and the procedure of 1(b) and 1(c) is followed one obtains the (5E) and (5Z) isomers of 12β-hydroxymethyl-6aβ,9β-methano-13,14,15,16,17,18,19,20-octanor-6a-carba-prostaglandin I$_2$, tetrahydropyranyl ether, and when the thus obtained (5Z) isomer is substituted for (5E)-12β-hydroxymethyl-9β-methyl-13,14,15,16,17,18,19,20-octanor-6a-carba-prostaglandin I$_2$, 11-tetrahydropyranyl ether in Example 1(d) and the procedure of Example 1(d) and 1(e) is followed one obtains (5Z)-12b-formyl-6aβ,9β-methano-13,14,15,16,17,18,19,20-octanor-6a-carba-prostaglandin I$_2$methyl ester, 11-tetrahydropyranyl ether.

(b) When in the procedure of Example 3(a) one substitutes the above obtained (5Z)-12β-formyl-6aβ,9β-methano derivative (5Z)-12β-formyl-9β-methyl-13,14,15,16,17,18,19,20-octanor-6a-carba-prostaglandin I$_2$ methyl ester, 11-tetrahydropyranyl ether and the procedure of Example 3(a) through 3(d) is followed there is obtained (5Z)-6-a$\beta$,9$\beta$-methano-15(R) and 15(S)-16(R,S)-16-methyl-18,19-tetradehydro-6a-carba-prostaglandin I$_2$.

EXAMPLE 6

When in the procedure of Example 2(c) 2-hexynoic acid, or 5-hexenoic acid is substituted for 2-methyl-4-hexynoic acid one obtains 2-oxo-hept-3-yne phosphonic acid dimethyl ester, and 2-oxo-hept-6-ene phosphonic acid dimethyl ester.

EXAMPLE 7

When in the procedure of Example 3(a) one substitutes each of the phosphonic acid dimethyl ester compounds from Example 6 for 3-methyl-2-oxohept-5-yne phosphonic acid dimethyl ester and (5Z)-12$\beta$-formyl-9$\beta$-methyl-13,14,15,16,17,18,19,20-octanor-6a-carba-prostaglandin I$_2$ methyl ester, 11-tetrahydropyranyl ether is substituted for the corresponding (5E) isomer used in Example 3(a) and the procedure of Example 3(a) through 3(d) is followed the following products are obtained:

(5Z)-9$\beta$-methyl-15(S)-16,17-tetradehydro-6a-carba-prostaglandin I$_2$ and (5Z)-9$\beta$-methyl-15(S)-19,20-dehydro-6a-carba-prostaglandin I$_2$.

FORMULAS

-continued
CHART B
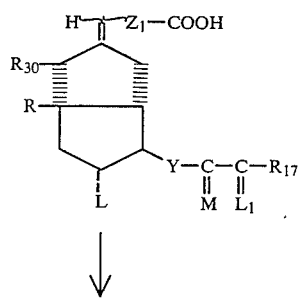
Formula B-2
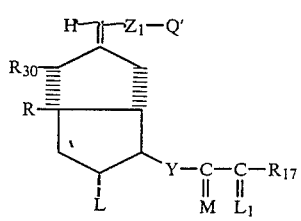
Formula B-3
CHART F
Formula A-2, Formula A-3 ---------→
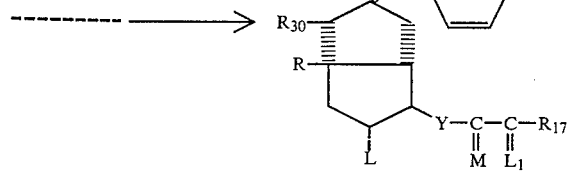
Formula F-1
$R_{21}O-CH_2-(CH_2)_g-$ <image without aldehyde>
Formula F-2
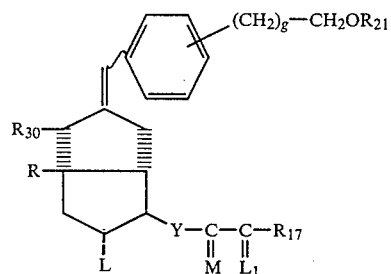
Formula F-4
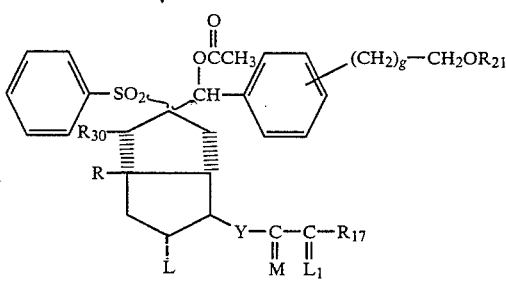
Formula F-3
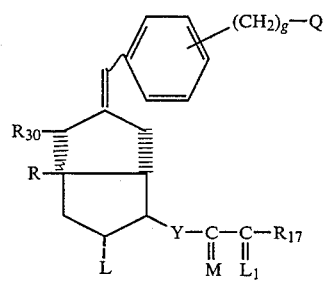
Formula F-5
CHART G
Formula A-2
and
Formula A-3
+ 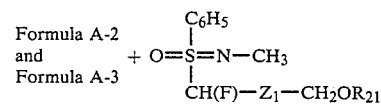
Formula G-1

-continued
CHART G

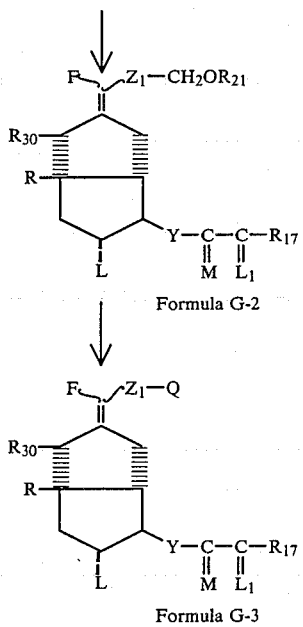

Formula G-2

Formula G-3

We claim:
1. A compound of the formula wherein R is $C_1$–$C_4$ alkyl; $R_{30}$ is hydrogen or $R_{30}$ and R taken together form a methylene moiety;
wherein D is cis $>C=C(R_3)-$, trans $>C=C(R_3)-$ or $>CHCH_2$, wherein $R_3$ is hydrogen or fluoro;
wherein Z is:
(1) $-CH_2-(CH_2)_f-C(R_4)_2-$ wherein each $R_4$ is the same and is hydrogen or fluoro, and f is zero, one, 2 or 3;
(2) trans$-CH_2-CH=CH-$; or
(3) $-(PH)-(CH_2)_g-$ wherein Ph is 1,2—, 1,3—, or 1,4-phenylene and g is zero, one, 2 or 3; with the proviso that when Z is $-(Ph)-(CH_2)_g-$, $R_3$ is hydrogen;
wherein Q is
(1) $-COOR_5$, wherein $R_5$ is
  (a) hydrogen,
  (b) ($C_1$-$C_{12}$)alkyl,
  (c) ($C_3$-$C_{10}$)cycloalkyl,
  (d) ($C_7$-$C_{12}$)aralkyl,
  (e) phenyl optionally substituted with one, 2 or 3 chloro or ($C_1$-$C_4$)alkyl,
  (f) phenyl substituted in the para-position with $-NHCOR_6$, $-COR_7$, $-OC(O)R_8$ or $-CH=N-NHCONH_2$, wherein $R_6$ is methyl, phenyl, acetamidophenyl, benzamidophenyl or $-NH_2$; $R_7$ is methyl, phenyl, $-NH_2$, or methoxy; and $R_8$ is phenyl or acetamidophenyl;
  (g) phthalidyl,
  (h) 3-(5,5-dimethyl-1,3,2-dioxaphosphorinan-2-yl)-2-oxopropan-1-yl P-oxide,
  (i) 3-(5,5-di(hydroxymethyl)-1,3,2-dioxaphosphorinan-2-yl)-2-oxopropan-1-yl P-oxide, or
  (j) a pharmacologically acceptable cation;
(2) $-CH_2OH$;
(3) $-COL_2$, wherein $L_2$ is
  (a) an amino group of the formula $-NR_9R_{10}$ wherein $R_9$ is hydrogen or ($C_1$–$C_{12}$)alkyl and $R_{10}$ is
    (i) hydrogen
    (ii) ($C_1$-$C_{12}$)alkyl
    (iii) ($C_3$-$C_{10}$)cycloalkyl,
    (iv) ($C_7$-$C_{12}$)aralkyl
    (v) phenyl optionally substituted with one, 2 or 3 chloro, ($C_1$-$C_3$)alkyl, hydroxy, carboxy, ($C_2$-$C_5$)alkoxycarbonyl, or nitro,
    (vi) ($C_2$-$C_5$)carboxyalkyl,
    (vii) ($C_2$-$C_5$)carbamoylalkyl,
    (viii) ($C_2$-$C_5$)cyanoalkyl,
    (ix) ($C_3$-$C_6$)acetylalkyl,
    (x) ($C_7$-$C_{12}$)benzoalkyl, optionally substituted by one, 2, or 3 chloro, ($C_1$-$C_3$)alkyl, hydroxy, ($C_1$-$C_3$)alkoxy, carboxy, ($C_2$-$C_5$)-alkoxycarbonyl, or nitro,
    (ix) pyridyl, optionally substituted by one, 2, or 3 chloro, ($C_1$-$C_3$)alkyl, or ($C_1$-$C_3$)alkoxy,
    (xii) ($C_6$-$C_9$)pyridylalkyl optionally substituted by one, 2, or 3 chloro, ($C_1$-$C_3$)alkyl, hydroxy, or ($C_1$-$C_3$)alkyl,
    (xiii) ($C_1$-$C_4$)hydroxyalkyl,
    (xiv) ($C_1$-$C_4$)dihydroxyalkyl,
    (xv) ($C_1$-$C_4$)trihydroxyalkyl;
  (b) cycloamine selected from the group consisting of pyrolidino, piperidino, morpholino, piperazino, hexamethyleneimino, pyrroline, or 3,4-didehydropiperidinyl optionally substituted by one or 2 ($C_1$-$C_{12}$)alkyl;
  (c) carbonylamino of the formula $-NR_{11}COR_{10}$, wherein $R_{11}$ is hydrogen or ($C_1$-$C_4$)alkyl and $R_{10}$ is other than hydrogen, but otherwise defined as above;
  (d) sulfonylamino of the formula $-NR_{11}SO_2R_{10}$, wherein $R_{11}$ and $R_{10}$ are defined in (c);
(4) $-CH_2NL_3L_4$, wherein $L_3$ and $L_4$ are hydrogen or ($C_1$-$C_4$)alkyl, being the same or different, or the pharmacologically acceptable acid addition salts thereof when Q is $-CH_2NL_3L_4$; or
(5) $-CN$;
wherein L is H,H; $\alpha-OR_{12},\beta-H$; $\alpha H,\beta-OR_{12}$; $\alpha-CH_2OR_{12},\beta-H$; $\alpha-H,\beta-CH_2OR_{12}$ wherein $R_{12}$ is hydrogen or a hydroxyl protective group;
wherein Y is trans $-CH=CH-$, cis$-CH=CH-$, $-CH_2CH_2-$, or $-C\equiv C-$;
wherein M is $\alpha-OR_{12},\beta-R_{14}$; or $\alpha-R_{14}, \beta-OR_{12}$, wherein $R_{12}$ is as defined above, and $R_{14}$ is hydrogen or methyl;
wherein $L_1$ is $\alpha-R_{15},\beta-R_{16}$; $\alpha-R_{16},\beta-R_{15}$; or a mixture thereof wherein $R_{15}$ and $R_{16}$ are hydrogen, methyl, or fluoro being the same or different with the proviso that one of $R_{15}$ and $R_{16}$ is fluoro only when the other of $R_{15}$ and $R_{16}$ is hydrogen or fluoro; wherein

taken together is

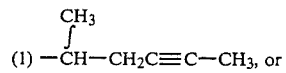

(2) —C≡C—$C_qH_{2q}CH_3$ where q is an integer of from 2 to 6, and individual optical isomers thereof.

2. A compound of claim 1 wherein $R_{12}$ is hydrogen or a pharmacologically acceptable salt thereof.

3. A compound of claim 2 wherein D is cis—C=C(R$_3$)— or trans—C=C(R$_3$)—.

4. A compound of claim 3 wherein $R_3$ is hydrogen and Y is —$CH_2CH_2$—, —C≡C— or trans—CH=CH—.

5. A compound of claim 4 wherein Z is —$CH_2(CH_2)_f$—$C(R_4)_2$— and Q is —$COOR_5$ or —$COL_2$ wherein $L_2$ is —$NR_9R_{10}$.

6. A compound of claim 5 wherein

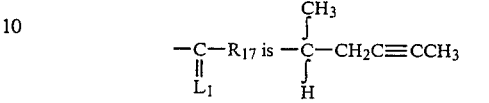

7. A compound of claim 6 wherein m is a α—$OR_{12}$,β—H.

8. A compound of claim 7 which is (5Z)-9β-methyl-15(S)-16(R,S)-16-methyl-18,19-tetradehydro-6a-carba-prostaglandin $I_2$.

9. A compound of claim 6 which is (5Z)-9βmethyl-15(R)-16(R,S)-16-methyl-18,19-tetradehydro-6a-carba-prostaglandin $I_2$.

* * * * *

UNITED STATES PATENT OFFICE
CERTIFICATE OF CORRECTION

Patent No. 4,533,749          Dated 6 August 1985

Inventor(s) P.A. Aristoff and J.C. Sih

It is certified that error appears in the above-identified patent and that said Letters Patent are hereby corrected as shown below:

Column 39, lines 45 and 46: "cis>C=C($R_3$)-, trans>C=C($R_3$)- or >CHCH$_2$" should read --cis$\geq$C=C($R_3$)-, trans$\geq$C=C($R_3$)- or $\geq$CHCH$_2$--.

Signed and Sealed this

Thirty-first Day of May, 1988

*Attest:*

DONALD J. QUIGG

*Attesting Officer*      *Commissioner of Patents and Trademarks*